(12) United States Patent
Fischer

(10) Patent No.: US 8,193,391 B2
(45) Date of Patent: Jun. 5, 2012

(54) PROCESS FOR PREPARATION OF 3-(2-HYDROXY-5-SUBSTITUTED PHENYL)-N-ALKYL-3-PHENYLPROPYLAMINES

(75) Inventor: Erik Fischer, Värlöse (DK)

(73) Assignee: Lek Pharmaceuticals, D.D., Ljubljana (SI)

( * ) Notice: Subject to any disclaimer, the term of this patent is extended or adjusted under 35 U.S.C. 154(b) by 564 days.

(21) Appl. No.: 12/305,913

(22) PCT Filed: Jun. 18, 2007

(86) PCT No.: PCT/EP2007/005357
§ 371 (c)(1),
(2), (4) Date: Feb. 20, 2009

(87) PCT Pub. No.: WO2007/147547
PCT Pub. Date: Dec. 27, 2007

(65) Prior Publication Data
US 2010/0234473 A1   Sep. 16, 2010

(30) Foreign Application Priority Data

Jun. 20, 2006 (EP) .................................... 06012619

(51) Int. Cl.
*C07C 215/00* (2006.01)
(52) U.S. Cl. ....................... 564/443; 564/316; 514/648
(58) Field of Classification Search ........................ None
See application file for complete search history.

(56) References Cited

U.S. PATENT DOCUMENTS

2010/0286446 A1 * 11/2010 Bonde-Larsen et al. ....... 564/316

FOREIGN PATENT DOCUMENTS

| CA | 2 618 446 A1 | 2/2007 |
| EP | 0 325 571 A1 | 7/1989 |
| WO | WO 94/11337 A1 | 5/1994 |
| WO | WO 98/43942 A1 | 10/1998 |
| WO | WO 03/002059 A2 | 1/2003 |
| WO | WO 2005/012227 A2 | 2/2005 |
| WO | WO/2007/017544 A2 | 2/2007 |

OTHER PUBLICATIONS

M. Gopalakrishnan: "Novel Carbon-Carbon Bond Formation between N-Methyl-3-phenyl-3-hydroxypropylamine and Cresols Catalyzed by p-Toluenesulphonic Acid." Synthetic Communications, vol. 36, Jul. 2006, pp. 1923-1926.

* cited by examiner

*Primary Examiner* — Sudhakar Katakam
(74) *Attorney, Agent, or Firm* — Arent Fox LLP

(57) ABSTRACT

A new process for preparation of 3-(2-hydroxy-5-substituted phenyl)-N,alkyl-3-phenylpropylamines from cinnamyl chloride via N-alkyl-3-phenylprop-2-en-1-amine has been developed.

26 Claims, No Drawings

PROCESS FOR PREPARATION OF 3-(2-HYDROXY-5-SUBSTITUTED PHENYL)-N-ALKYL-3-PHENYLPROPYLAMINES

CROSS-REFERENCE TO RELATED APPLICATION

This application is a National Stage entry of International Application No. PCT/EP2007/005357, filed Jun. 18, 2007, which claims priority to European Patent Application No. 06012619.0 filed Jun. 20, 2006, the entire specification claims and drawings of which are incorporated herein by reference.

TECHNICAL FIELD

The invention belongs to the field of organic chemistry and relates to a novel efficient synthetic process for the preparation of substituted 3-(2-hydroxy-5-methylphenyl)-N-alkyl-3-phenylpropylamines, such as 3-(2-hydroxy-5-methylphenyl)-N,N-diisopropyl-3-phenylpropylamine.

BACKGROUND ART

By our process one can synthesize 3,3-diphenylpropyl amines, such as those known from EP 325571. Those compounds may be tertiary or secondary amines.

Several synthetic approaches for preparation of such compounds have been described. For example 3-(2-hydroxy-5-methylphenyl)-N,N-diisopropyl-3-phenylpropylamine may be prepared using relatively long synthetic sequence or special equipment. If desired, enantiomerically pure product is obtained either with the resolution of the enantiomers in the last step or the chiral synthesis.

However there is still a need for shorter, less expensive and more industrially applicable processes performed under milder conditions still remains.

Representative compound prepared according to our process: (+)-(R)-3-(2-hydroxy-5-methylphenyl)-N,N-diisopropyl-3-phenylpropylamine, currently marketed as (+)-L-tartrate salt is an important urological drug, which acts as a selective muscarinic receptor antagonist. It is used for manufacturing of the medicament for treating the patients with overactive bladder showing symptoms of urinary frequency, urgency, or urge incontinence and can be used for treating asthma, COPD and allergic rhinitis. Also its metabolite a 5-hydroxymethyl compound exhibits antimuscarinic activity. Same 3,3-diphenylpropyl amines structure is also found in some other drugs, and those compounds obtained by our process may be used for manufacturing the medicament, when they are combined with a pharmaceutically acceptable carrier.

DISCLOSURE OF THE INVENTION

In the most general aspect the invention provides a process for preparing a compound of formula III'

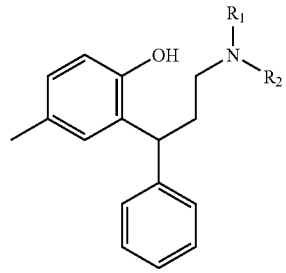

where $R_1$ is selected from: H, $C_1$-$C_3$ alkyl; $R_2$ is selected from $C_1$-$C_3$ alkyl, and $R_3$ is selected from $CH_3$, Cl, Br, I, CHO, or CN, or a salt thereof, characterized in that compound of formula II

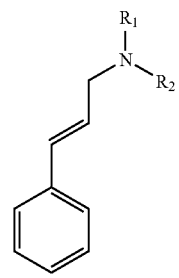

where $R_1$ and $R_2$ are defined as above
is reacted with compound of formula I

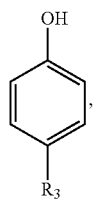

wherein $R_3$ is selected from $CH_3$, Cl, Br, I, CHO, or CN.
Specifically compound of formula III' is in one aspect further converted into compound of formula IV

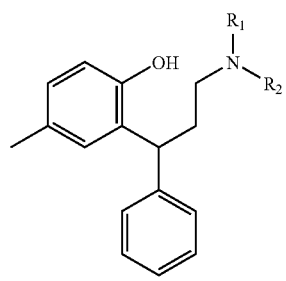

where $R_1$ is selected from: H, $C_1$-$C_3$ alkyl; and $R_2$ is selected from $C_1$-$C_3$ alkyl, or a salt thereof. The compound can be isolated as a mixture of enantiomers which is subsequently optically resolved and optionally purified, and which is subsequently formulated into pharmaceutical together with a pharmaceutically acceptable carrier.

In another aspect the invention represents a process for preparing a compound of formula III

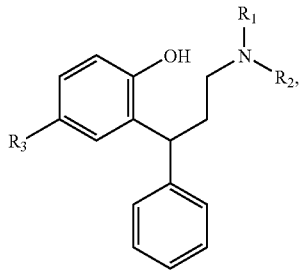

where $R_1$ is selected from: H, $C_1$-$C_3$ alkyl; and $R_2$ is selected from $C_1$-$C_3$ alkyl, preferably $R_1$ is hydrogen or isopropyl and $R_2$ is methyl or isopropyl, more preferably $R_1$ and $R_2$ are isopropyl, or a salt thereof, preferably tartrate salt, characterized in that compound of formula II

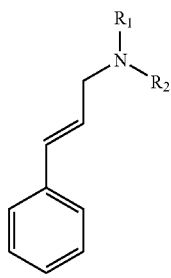

where $R_1$ and $R_2$ are defined as above is reacted with p-cresol.

The process is in general performed in presence of an acid and followed by isolation by extraction into an organic solvent and conversion into salt.

In an aspect the above compound of formula II is prepared by reacting an amine of formula VI

where $R_1$ and $R_2$ are defined as above, with cinnamyl halide, which is preferably chloride, or alternatively with cinnamaldehyde and a hydride reducing agent, which is preferably lithium, sodium or potassium borohydride, or cyanoborohydride.

Said reaction for preparation of compound of formula II is preferably performed in presence of base at room temperature in solvents suitable for amination or reductive amination.

In an aspect the above compound formula II is prepared by vicinal elimination of substituents $Y_1$ and $Y_2$ from the compound of formula V

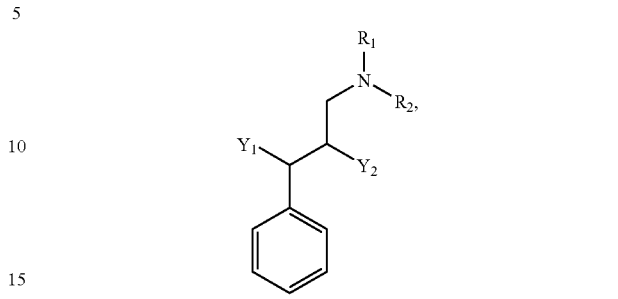

where $Y_1$ and $Y_2$ are substituents that can be eliminated, and are preferably both $Y_1$ and $Y_2$ are halogens or $Y_2$ is hydrogen and $Y_1$ is hydroxy or halogen.

In a specific aspect the compound of formula II is not isolated and alternatively is formed in-situ.

Generally in the process of our invention, the mixture of enantiomers of compound of formula III is optically resolved, preferably by salt formation with an optically active organic acid or alternatively by chromatography.

Specifically our invention is a process for preparing N,N-diisopropyl-3-(2-hydroxy-5-methylphenyl)-3-phenylpropyl amine or a salt thereof characterized in that it comprises following steps:
a) providing N,N-diisopropyl-3-phenylprop-2-en-1-amine;
b) reacting N,N-diisopropyl-3-phenylprop-2-en-1-amine with p-cresol to give N,N-diisopropyl-3-(2-hydroxy-5-methylphenyl)-3-phenylpropyl amine;
c) (optionally) isolating the obtained compound of previous step; and
d) optically resolving the mixture of enantiomers of N,N-diisopropyl-3-(2-hydroxy-5-methylphenyl)-3-phenylpropyl amine by conversion into a salt of tartaric acid wherein more specifically N,N-diisopropyl-3-phenylprop-2-en-1-amine is provided by amination of cinnamyl halide or reductive amination of cinnamaldehyde or by elimination of water from 3-hydroxy-N,N-diisopropyl-3-phenylpropan-1-amine.

Industrial aspect of the invention is also a process for making a pharmaceutical composition comprising a compound of formula III

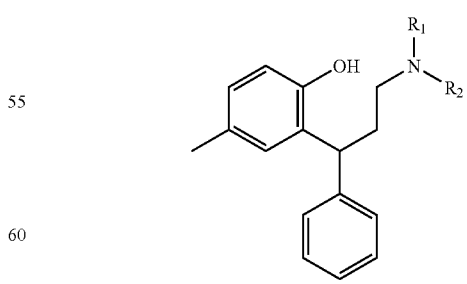

where $R_1$ is selected from: H, $C_1$-$C_3$ alkyl; and $R_2$ is selected from $C_1$-$C_3$ alkyl or a salt thereof, preferably (+)-N,N-diisopropyl-3-(2-hydroxy-5-methylphenyl)-3-phenylpropylamine hydrogen tartrate;

where said compound has been prepared as described above, wherein said compound is in a process step incorporated into a pharmaceutical composition together with a pharmaceutically acceptable carrier, which may be done by tableting or preparing a granulate or pellets which are filled into capsules.

An aspect of the invention is the use of compound prepared as above disclosed in the process of preparing a medicament.

DETAILED DESCRIPTION OF THE INVENTION

The process comprises the steps of:

a) reacting an amine of formula $HNR_1R_2$, where $R_1$ and $R_2$ are as defined above, preferably diisopropyl amine, with cinnamyl halide; or in alternative embodiment with cinnamaldehyde and suitable reducing reagent (reductive amination) and b) reacting thus obtained compound with p-cresol, and c) optionally optically resolving the mixture of enantiomers obtained in previous step. In case the aminating agent used in step a) is different from diisopropylamine the formed compound can be optionally converted to another amine, preferably diisopropylamine, and isolating the desired compound and is depicted on following Scheme 1:

Scheme 1

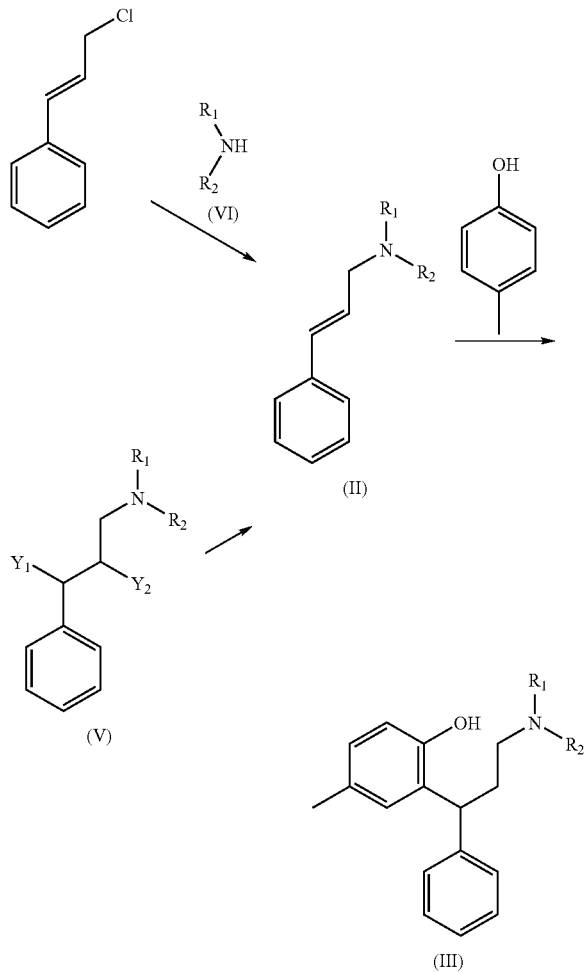

In a specific embodiment, in above step a) cinnamyl halide is preferably chloride, but also bromide or iodide; or a halo substituted alkanesulphonate, preferably methanesulphonate; or trifluoromethanesulphonate or arenesulphonate, preferably tosylate; or another analogue with easily removed group, which are considered equivalent.

In said alternative reductive amination, a suitable reducing agent is preferably alkali metal borohydride, more preferably selected from lithium, sodium or potassium borohydride, cyanoborohydride or triacetoxyborohydride, most preferably sodium cyanoborohydride. This embodiment is especially suitable for reductive amination with an amine of formula $HNR_1R_2$, where $R_1$ is hydrogen and $R_2$ as defined above.

In an alternative embodiment the compound to be reacted in step b) with p-cresol is obtained by vicinal elimination of 2,3 substituents on the compound of the amine of formula V, where $Y_1$ and $Y_2$ are substituents that can be eliminated by an acid or preferably by base catalyzed elimination. Preferably the compound If formula V is 2,3-dihalo substituted or 3-halo substituted amine where $R_1$ and $R_2$ are as defined above, more preferably $Y_1$ is hydroxyl and $Y_2$ is hydrogen from which water is eliminated by a base such as NaOH, in a suitable apolar solvent. The specific preferred compounds of formula V are 3-bromo-N,N-diisopropyl-3-phenylpropan-1-amine and 3-hydroxy-N,N-diisopropyl-3-phenylpropan-1-amine. Under certain conditions this and subsequent reaction may be conducted in a single vessel and the intermediate compound II is not isolated or is formed in situ.

Most preferably or most preferably water elimination intermediates like 3-hydroxy-N,N-diisopropyl-3-phenylpropan-1-amine, which may be conveniently prepared from simple compounds by reacting acetophenone and formaldehyde with an amine of formula $HNR_1R_2$, where $R_1$ and $R_2$ are as defined above, preferably diisopropylamine and subsequent reduction of obtained compound.

The reaction steps a) and b) may proceed with substituted cinnamyl derivatives.

More generally in accordance with our invention also derivatives may be prepared, especially 5-hydroxymethyl substituted derivatives.

The process in general thus comprises the steps of:

a) reacting an amine of formula $HNR_1R_2$, where $R_1$ and $R_2$ are as defined above, preferably diisopropyl amine, with cinnamyl halide; or in alternative embodiment with cinnamaldehyde and suitable reducing reagent (reductive amination) and b) reacting thus obtained compound with compound of formula I

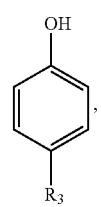

wherein $R_3$ is either $CH_3$, or X (where X is Br, Cl, or I), CHO, or CN and c) optionally optically resolving the mixture of enantiomers obtained in previous step. In case the aminating agent used in step a) is different from diisopropylamine the formed compound can be optionally converted to another amine, preferably diisopropylamine, and d1) where $R_3$ is Br, Cl, or I, protecting the obtained compound of formula III', subjecting obtained compound to conditions of Grignard reaction in DMF or another N,N-disubstituted formamide giving (N,N-diisopropyl-3-phenyl-3-(5-formyl-2-hydroxyphenyl)propan-1-amine (IV', $R_3$=CHO), and reducing to give the compound of formula IV; or d2) where $R_3$ is CHO, reducing to give the compound of formula IV; or d3) where $R_3$ is CN, hydrolyzing the obtained compound of formula III', and reducing to give the compound of formula IV;

d4) where $R_3$ is CN, reducing the obtained compound of formula III', to give the compound of formula IV' (R=CHO), and further reduced it to the compound of formula IV and isolating the desired compound and is depicted on following Scheme 2:

Scheme 2

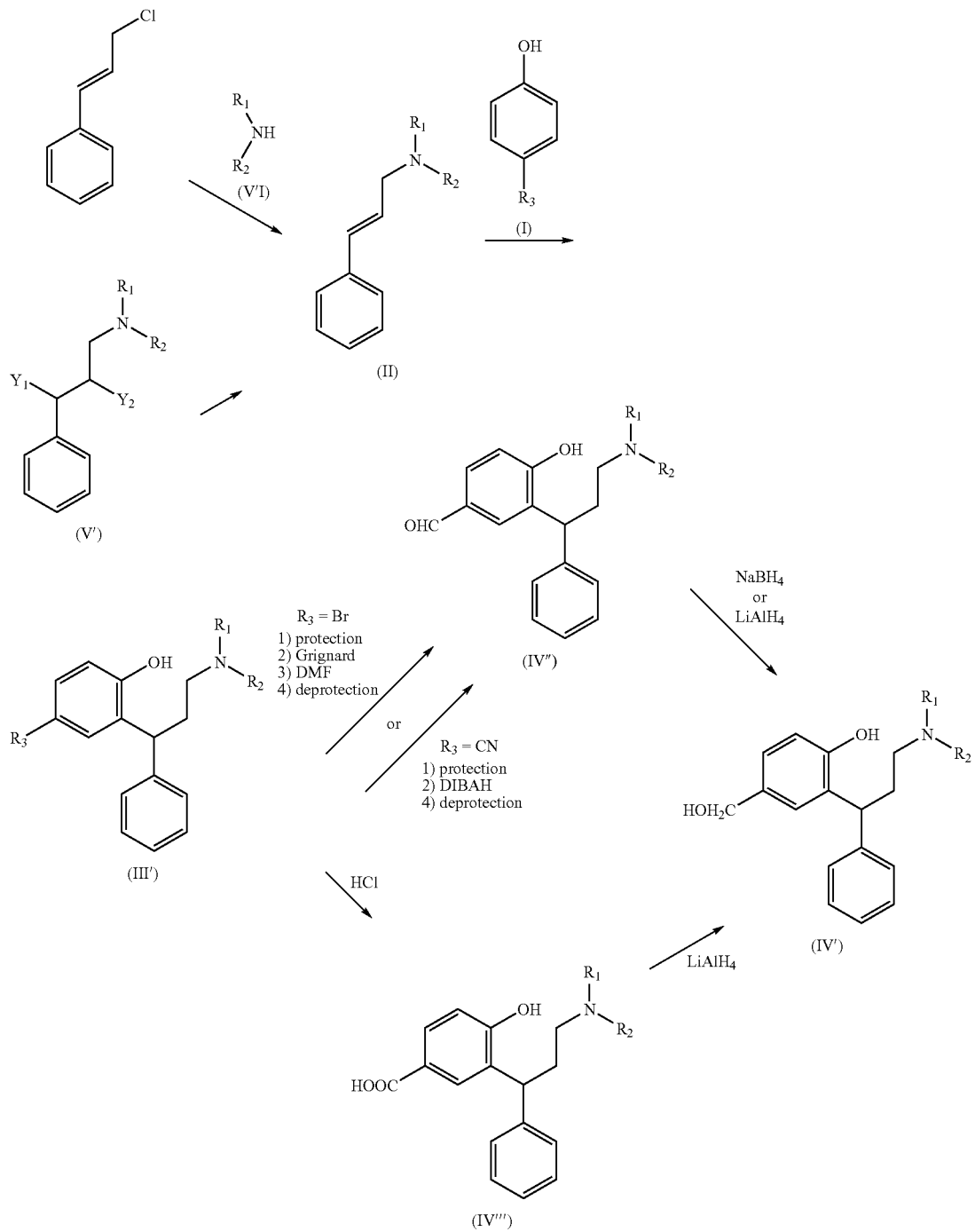

In the preferred embodiment the reaction sequence is as follows

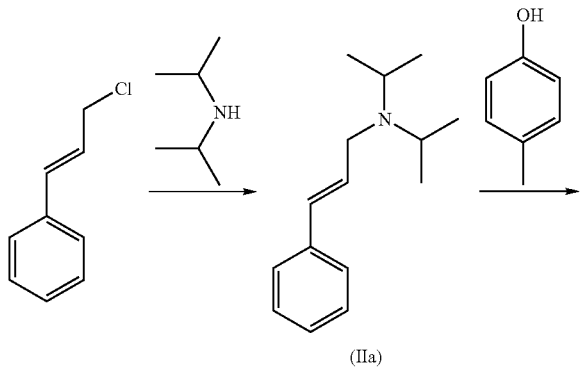

(IIa)

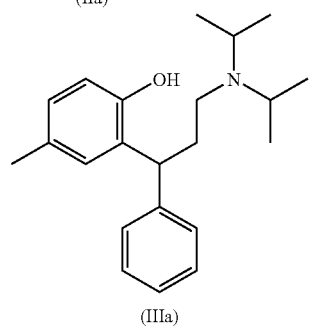

(IIIa)

In the preferred embodiment the process starts with a reaction of cinnamyl chloride with amine, preferably primary or secondary amine having $C_1$ to $C_3$ alkyl substituents, preferably diisopropyl amine in presence of a base, preferably inorganic, more preferably potassium carbonate. The use of an additional base is highly preferable as use of an excess of reacting amines as a base is not cost effective and may cause ecological problems. Suitable solvents are selected from the group of alcohols, acetonitrile, esters, ethers or aromatic hydrocarbons, preferably mixture of toluene and methanol. The reaction proceeds for up to 1 day at room temperature.

An important step of our process is subsequent reaction of the obtained compound II with p-cresol or equivalently with phenol, o-cresol, m-cresol but also other substituted phenols, in presence of an acid, preferably in an organic acid, preferably methanesulfonic acid at an elevated temperature, preferably at 80 to 200° C., more preferably at 120 to 130° C., for up to one day. Preferably the p-cresol functions also as a solvent.

Subsequent isolation of the obtained compound is preferably done by adding water and an organic solvent not miscible with water, preferably toluene to the reaction mixture, adjusting pH to about 9.5, distilling said solvents off and upon dissolving in a suitable solvent, preferably isopropanol, adding a suitable optically active carboxylic acid and a formic acid, preferably from 0.5 to 0.6 molar equivalents of each, preferably 0.55 equivalents of each, stirring the mixture for up to one day, whereupon the product is isolated and optionally recrystallized.

The preferable workup is by treating the compound (III) with (+)-L-tartaric acid to achieve resolution of the enantiomers. The resolution of enantiomers will however mean to include also any other usual method. The following examples are offered to illustrate aspects of the present invention, and are not intended to limit or define the present invention in any manner.

Example 1

Preparation of Compound of Formula III', where $R_1$ and $R_2$ are Both iPr, and $R_3$ is Me 51 g cinnamyl chloride is reacted with 50 g diisopropyl amine in presence of 41 g potassium carbonate in 100 ml toluene containing 25 ml methanol and after 24 hours reflux, 96% conversion is observed. Addition of water and separating the phases, and subsequent washing and evaporation leaves a quantitative amount of the amine (72.8 g).

Example 2

Preparation of Compounds of Formula III', where $R_1$ is H and $R_2$ an Alkyl or Aryl, and $R_3$ is Me 51 g cinnamyl chloride is reacted with 27 g isopropyl amine in presence of 40 g potassium carbonate in 100 ml toluene containing 25 ml methanol) for 1 day. Addition of water and separating the phases, and subsequent washing and evaporation leaves a quantitative amount of the amine. In a similar manner reacting cinnamyl chloride with equimolar amounts of methylamine or phenylamine yields corresponding amines.

Example 3

Alternative Preparation of Compound of Formula III', where $R_1$ and $R_2$ are Both iPr, and $R_3$ is Me 20.0 g of acetophenone is reacted with 18.7 g of diisopropylamine and 40 ml of water solution of formaldehyde in presence of 20 ml of conc. HCl in 360 ml of methanol for 2 hours at reflux temperature. After evaporation of most of methanol water and ethylacetate is added. After separation the organic phase was concentrated by evaporation and diluted with methanol. The dissolved compound is reduced with 4.2 g of sodium borohydride to yield 3-hydroxy-N,N-diisopropyl-3-phenylpropan-1-amine which may be converted into N,N-diisopropyl-3-phenylpropyl-2-ene-1-amine by treating with strong alkali.

Example 4

Preparation of Compound of Formula IIIa, where $R_1$ and $R_2$ are Both iPr, and $R_3$ is Me 10.2 g of N,N-diisopropyl-3-phenylprop-2-en-1-amine, is added 20.5 g p-cresol and 15.8 g methanesulfonic acid and heated to 130° C. for 6 hours. Chromatography shows disappearance of the peak corresponding N,N-diisopropyl-3-phenylprop-2-en-1-amine, and a fine peak at the retention time of 3-(2-hydroxy-5-methylphenyl)-N,N-diisopropyl-3-phenylpropylamine. From the reaction mixture the (+)-(R)-3-(2-hydroxy-5-methylphenyl)-N,N-diisopropyl-3-phenylpropylamine is isolated as follows: Water and toluene (200 ml each) are added to the reaction mixture and pH adjusted to 9.5. The toluene layer is isolated and washed with water. Distilling off the toluene leaves an oily mass. This is taken up in 300 ml 2-propanol, added 0.55 eq tartaric acid and 0.55 eq formic acid, After stirring overnight, the suspension is filtered. The wet filter cake is approximately 97% pure. The wet filter cake is taken up in 300 ml 2-propanol and heated to reflux, cooled to 5° C., filtered and dried (yield 85%). Purity on HPLC (achiral) 99.5%.

Example 5

Preparation of Compound of Formula III, where $R_1$ is H and $R_2$ is Me, and $R_3$ is Me 7.5 g of N-methyl-3-phenylprop-2-en-1-amine is added 20.5 g p-cresol and 15.8 g methanesulfonic acid and heated to 125° C. for 8 hours. From the reaction mixture the (+)-(R)-3-(2-hydroxy-5-methylphenyl)-N-methyl-3-phenylpropylamine is isolated by addition of water and toluene and extraction to toluene and addition of 0.6 eq tartaric acid and 0.6 eq formic acid and crystallizing and recrystallizing till e.e. exceed 99.5%.

Example 6

Alternative Preparation of Compound of Formula IIIa, where $R_1$ and $R_2$ are Both iPr, and $R_3$ is Me 5.2 g of N,N-diisopropyl-3-hydroxy-3-phenylpropan-1-amine was added to the mixture of 20 ml 40% sol of NaOH and 10 ml methanol and heated to 50° C. for 40 min. The mixture was diluted with 50 ml of toluene, water phase was separated and toluene fraction was concentrated. 10.3 g of p-cresol and 15.8 g methanesulfonic acid is added to concentrate and the mixture is heated to 130° C. for 8 hours. The resulted mixture is further treated as described in the previous example to yield title product in the form tartrate in 64% yield (purity 99.1%).

Example 7

Preparation of Compound of Formula III', where $R_1$ and $R_2$ are Both iPr, and $R_3$ is Cl 2.04 g of N,N-diisopropyl-3-phenylprop-2-en-1-amine is added to 4.86 g α-chlorophenol and 3.1 g methanesulfonic acid and heated to 130° C. for 8 hours. The mixture is cooled down, water (30 ml) and toluene (400 ml) are added to the reaction mixture and pH adjusted to 9.5. The toluene layer is isolated and washed with water. Distilling off the toluene leaves an oily mass. This is taken up in 50 ml ethanol, added 28 eq tartaric acid. After stirring overnight, the suspension is filtered. The wet filter cake is taken up in 60 ml 2-propanol and heated to reflux, cooled to 5° C., filtered and dried ((R)—N,N-diisopropyl-3-phenyl-3-(5-chloro-2-hydroxyphenyl)propan-1-amine tartrate, yield 65%, e.e. 98%).

Example 8

Preparation of Compound of Formula III', where $R_1$ and $R_2$ are Both iPr, and $R_3$ is Br 3.57 g of N,N-diisopropyl-3-phenylprop-2-en-1-amine, is added 11.5 g α-bromophenol and 5.5 g methanesulfonic acid and heated to 150° C. for 8 hours. The mixture is cooled down, water and toluene (70 ml each) are added to the reaction mixture and pH adjusted to 9.5. The toluene layer is isolated and washed with water. Distilling off the toluene leaves an oily mass. This is taken up in 100 ml 2-propanol, added 0.19 eq tartaric acid and 0.19 eq formic acid. After stirring overnight, the suspension is filtered. The wet filter cake is taken up in 60 ml 2-propanol and heated to reflux, cooled to 5° C., filtered and dried ((R)—N,N-diisopropyl-3-phenyl-3-(5-bromo-2-hydroxyphenyl)propan-1-amine tartrate, yield 82%, e.e. 98%).

Example 9

Preparation of Compound of Formula III', where $R_1$ and $R_2$ are Both iPr, and $R_3$ is CN 20.4 g of N,N-diisopropyl-3-phenylprop-2-en-1-amine is added to 53.5 g α-cyanophenol and 35.1 g ethanesulfonic acid and heated to 130° C. for 6 hours. The mixture is cooled down, water (300 ml) and toluene (350 ml) are added to the reaction mixture and pH adjusted to 9.5. The toluene layer is isolated and washed with water. Distilling off the toluene leaves an oily mass. This is taken up in 500 ml ethanol, added 280 eq tartaric acid. After stirring overnight, the suspension is filtered. The wet filter cake is taken up in 600 ml ethanol and heated to reflux, cooled to 5° C., filtered and dried ((R)—N,N-diisopropyl-3-phenyl-3-(5-cyano-2-hydroxyphenyl)propan-1-amine tartrate, yield 67%, e.e. 97%).

Example 10

Preparation of Compound of Formula IV', where $R_1$ and $R_2$ are Both iPr, and $R_3$ is CHO a) (R)—N,N-diisopropyl-3-phenyl-3-(5-cyano-2-hydroxyphenyl)propan-1-amine tartrate prepared as described in the previous example is recrystallized twice from ethanol to reach 99.9% e.e, the product is dissolved in ether, shaken three times with $NaHCO_3$ solution, ether dried over $MgSO_4$ and evaporated to give a compound in a form of base as yellow oil.
b) To a stirred solution of triisopropylsilyl chloride (26 ml) in anhydrous 1,2-dichloroethane (150 ml) is added 16.7 g of imidazole and 26.0 (R)—N,N-diisopropyl-3-phenyl-3-(5-cyano-2-hydroxyphenyl)propan-1-amine. The reaction is refluxed for 30 min and then is stirred overnight at room temperature, then 0.5 M HCl is added, layers are separated and the aqueous phase is extracted with ether. Combined organic fractions are washed with saturated $NaHCO_3$, dried over $MgSO_4$ filtered and solvents are evaporated to silylated product as brownish oil
c) The obtained silylated product is dissolved in 100 ml of dichloromethane absolute at a temperature between 0° C. and −5° C. in argon atmosphere, 120 ml of diisobutylaluminium hydride (DIBAL-H) (1M in n-hexane, 50 mmol) is added in a period of 3 hours. Reaction mixture was poured in a mixture of 500 g of ice and 100 ml of 6 M hydrochloric acid and stirred at room temperature for 1 h. Layers were separated and the water layer is reextracted twice with 120 ml of ethyl ether. Combined organic layers are washed with 120 ml of 5% solution of $NaHCO_3$ and 50 ml of brine successively. After drying over $MgSO_4$ and evaporating under reduced pressure giving (R)—N,N-diisopropyl-3-phenyl-3-(5-formyl-2-triisopropylsilyloxyphenyl)propan-1-amine as an oily residue.
d) A solution of protected formyl derivative (25 g, 0.06 mol) and triethylamine trihydrofluoride (9 ml, 0.06 mol) in 20 ml THF is stirred overnight and then cooled to −5° C. and quenched with cautious addition of potassium carbonate (11 g) in water (30 ml). The mixture was extracted with ether, dried over $MgSO_4$, evaporate to give (R)—N,N-diisopropyl-3-phenyl-3-(5-formyl-2-hydroxyphenyl)propan-1-amine as crude oil (44% from

13

III', R$_3$ is cyano) which could be further purified by chromatography (silica gel, chloroform-methanol 5:1 v/v) to give solid material.

Example 11

Preparation of Compound of Formula IV', where R$_1$ and R$_2$ are Both iPr, and R$_3$ is CHO (R)—N,N-diisopropyl-3-phenyl-3-(5-bromo-2-triisopropylsilyloxyphenyl)propan-1-amine (4.7 g), prepared by Example 10a and 10b, is dissolved in 30 ml freshly distilled THF, 0.06 g of iodine and 1.0 g of magnesium are added. The reaction mixture is refluxed in an argon atmosphere for 4 h. To the obtained Grignard reagent, 3 ml of anhydrous DMF is slowly added at 0° C. The reaction mixture was stirred for 2 h and overnight at room temperature and quenched with saturated ammonium chloride and the organic layer is separated from the aqueous layer. The aqueous layer is washed twice with diethyl ether (30 ml each), dried and evaporated to oil which is deprotected and purified as described I in Example 6. Yield 36% form III', R$_3$ is Br.

Example 12

Preparation of Compound of Formula IV', where R$_1$ and R$_2$ are Both iPr, and R$_3$ is CHO 2.04 g of N,N-diisopropyl-3-phenylprop-2-en-1-amine is added to 4.76 g p-hydroxybenzaldehyde and 3.1 g methanesulfonic acid and heated to 130° C. for 8 hours. The mixture is cooled down, water (30 ml) and toluene (400 ml) are added to the reaction mixture and pH adjusted to 9.5. The toluene layer is isolated and washed with water. Distilling off the toluene leaves an oily mass, which is purified by chromatography in silica gel, first by dichloromethane-diethyl ether, than chloroform-methanol 5:1 and crystallized in ethyl acetate-hexane to R,S—(R)—N,N-diisopropyl-3-phenyl-3-(5-formyl-2-hydroxyphenyl)propan-1-amine (yield 8%).

Example 13

Preparation of Compound of Formula IV, where R$_1$ and R$_2$ are Both iPr, and R$_3$ is CH$_2$OH A solution of (R)—N,N-diisopropyl-3-phenyl-3-(5-formyl-2-hydroxyphenyl)propan-1-amine, prepared by Example 10 (1.82 g) in THF (10 ml) is slowly added to a suspension of LiAlH$_4$ (0.13 g and the mixture is stirred for further 2 h. After cooled to 0° C. 0.2 ml of water and then 0.2 ml 10% NaHCO$_3$ is carefully dropped to the mixture, inorganic material is then filtered off and washed with fresh THF. Combined fractions are evaporated, the residue is dissolved in ethyl acetate, the solution is washed with 10% NaHCO$_3$, dried over MgSO$_4$ evaporated and the residue is crystallized from ethyl acetate to give a yellowish solid material (Yield 73%, m. p. 100-102° C.).

Example 14

Preparation of Compound of Formula IV, where R$_1$ and R$_2$ are Both iPr, and R$_3$ is CH$_2$OH The title compound can also be prepared from (R)—N,N-diisopropyl-3-phenyl-3-(5-formyl-2-hydroxyphenyl)propan-1-amine by reduction with sodium borohydride in methanol in 74% yield.

Example 15

Preparation of Compound of Formula IV, where R$_1$ and R$_2$ are Both iPr, and R$_3$ is CH$_2$OH (R)—N,N-diisopropyl-3-phenyl-3-(5-carboxy-2-hydroxyphenyl)propan-1-amine is prepared from (R)—N,N-diisopropyl-3-phenyl-3-(5-cyano-2-hydroxyphenyl)propan-1-amine tartrate by hydrolysis with 20% HCl in 6 h at 60° C., (yield 80%, m.p. 140-143° C.).

A solution of said carboxy compound 51.82 g, extra dried over P$_2$O$_5$ in vacuo for two days, in THF (10 ml) is slowly added to a suspension of LiAlH$_4$ (0.23 g and the mixture is stirred for further 2 h. After cooled to 0° C. 0.2 ml of water and then 0.2 ml 10% NaHCO$_3$ is carefully dropped to the mixture, inorganic material is then filtered off and washed with fresh THF. Combined fractions are evaporated, the residue is dissolved in ethyl acetate, the solution is washed with 10% NaHCO$_3$, dried over MgSO$_4$ evaporated and the residue is crystallized from ethyl acetate to give a yellowish solid material (Yield 55%, m. p. 101-102° C.).

The invention claimed is:

1. A process for preparing an acid addition salt of an optically active organic acid and a compound of formula III'

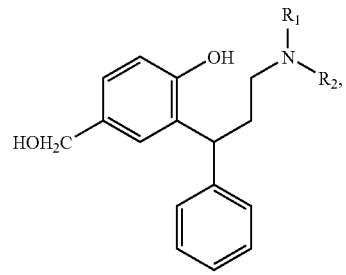

where R$_1$ is selected from the group consisting of: H, and C$_1$-C$_3$ alkyl; and R$_2$ is selected from the group consisting of C$_1$-C$_3$ alkyl;

or a salt thereof, comprising the steps of:

a) providing a compound of formula II

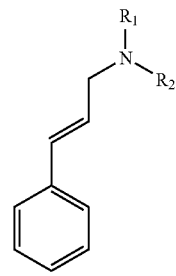

where $R_1$ and $R_2$ are defined as above;

b) reacting compound of formula II with compound of formula I

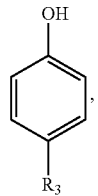

wherein $R_3$ is selected from the group consisting of $CH_3$, Cl, Br, I, CHO, and CN, in the presence of an acid; and c) optically resolving the crude product obtained in step b) by adding an optically active organic acid to the non-purified reaction product obtained in step b) in order to obtain the acid addition salt of an optically active organic acid and compound of formula III' wherein the overall yield of the optically active organic acid salt of compound of formula III' is at least 65% and the optical purity of the compound is at least 97% ee.

2. The process according to claim 1 wherein the compound of formula is further converted into compound of formula IV

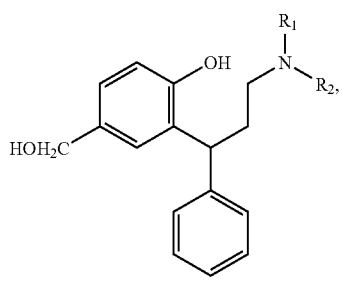

where $R_1$ is selected from the group consisting of: H, and $C_1$-$C_3$ alkyl; and $R_2$ is selected from the group consisting of $C_1$-$C_3$ alkyl; or a salt thereof.

3. The process according to claim 2 where in the compound of formula III', $R_3$ is Br, or Cl and the conversion to form the compound of formula IV is performed by subjecting the compound of formula III' to a Grignard reaction carried out in DMF to convert $R_3$ to CHO, followed by reduction.

4. The process according to claim 2 where in the compound of formula III', $R_3$ is CHO, and the conversion to form the compound of formula IV is performed by reduction.

5. The process according to claim 2 where in the compound of formula III', $R_3$ is CN, and the conversion to form the compound of formula IV is performed by hydrolysis and reduction.

6. The process according to claim 2 where in the compound of formula III', $R_3$ is CN, and the conversion to form the compound of formula IV is performed by reduction.

7. The process according to claim 3 where the reduction is performed with a hydride reduction reagent.

8. The process according to claim 7 where the hydride reduction reagent is selected from the group consisting of $LiAlH_4$ and $NaBH_4$.

9. The process according to claim 8 wherein the compound of formula IV

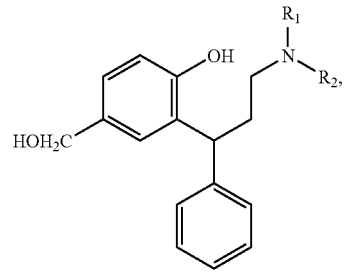

where $R_1$ is selected from the group consisting of: H, and $C_1$-$C_3$ alkyl; and $R_2$ is selected from the group consisting of $C_1$-$C_3$ alkyl, is isolated as a mixture of enantiomers which is subsequently optically resolved.

10. The process according to claim 1 where $R_3$ is $CH_3$.

11. The process according to claim 1, where the hydroxyl group is protected to form the compound of formula

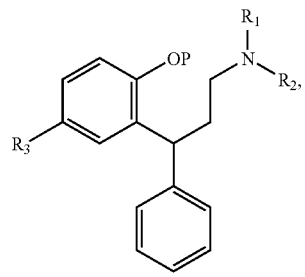

wherein P is a protecting group.

12. The process according to claim 11, where the protected hydroxyl group is subsequently deprotected.

13. The process according to claim 11, where the protecting group is a silyl protecting group.

14. A process according to claim 1 where the compound of formula II is prepared by reacting an amine of formula VI

where $R_1$ and $R_2$ are defined as above, with cinnamyl halide or with cinnamaldehyde and a hydride reducing agent.

15. A process according to claim 1 where the compound of formula II is prepared by vicinal elimination of substituents $Y_1$ and $Y_2$ from the compound of formula V

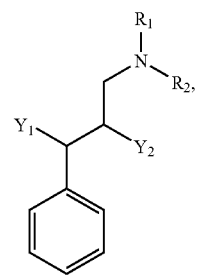

where $Y_1$ and $Y_2$ are substituents that can be eliminated.

16. The process according to claim 15 where both $Y_1$ and $Y_2$ are halogens or $Y_2$ is hydrogen and $Y_1$ is hydroxy or halogen.

17. The process according to claim 1 where the compound of formula II is formed in situ.

18. The process according to claim 1 where the mixture of enantiomers of compound of formula III' is optically resolved.

19. The process according to claim 1 where $R_1$ and $R_2$ are both isopropyl.

20. The process according to claim 1, wherein $R_1$ and $R_2$ is isopropyl, respectively, and $R_3$ is methyl, and the optically active organic acid added in step c) is tartaric acid.

21. A process for making a pharmaceutical composition comprising a compound of formula III

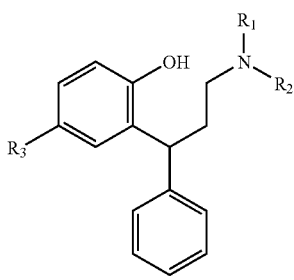

where $R_1$ is selected from the group consisting of: H, and $C_1$-$C_3$ alkyl; and $R_2$ is selected from the group consisting of $C_1$-$C_3$ alkyl or a salt thereof, where said compound has been prepared according to the process of claim 1, and wherein said compound is incorporated into a pharmaceutical composition together with a pharmaceutically acceptable carrier.

22. A method of manufacturing a medicament, comprising providing a compound prepared according to claim 9 or a salt thereof and a pharmaceutically acceptable carrier, and combining the compound and carrier to form a medicament.

23. A pharmaceutical composition comprising a compound prepared according to claim 9 or a salt thereof together with a pharmaceutically acceptable carrier.

24. The process according to claim 9, wherein the mixture of optically resolved enantiomers is purified.

25. The process of claim 20, further comprising isolating the N,N-diisopropyl-3-(2-hydroxy-5-methylphenyl)-3-phenylpropyl amine obtained in step (b) prior to conducting optical resolving step (c).

26. The process of claim 21, wherein the compound is (+)-N,N-diisopropyl-3-(2-hydroxy-5-methylphenyl)-3-phenylpropylamine hydrogen tartrate.

* * * * *